US012708665B2

(12) United States Patent
Saffitz

(10) Patent No.: US 12,708,665 B2
(45) Date of Patent: Aug. 18, 2026

(54) ANTI-IL-1β ANTIBODY THERAPY IN ARRHYTHMOGENIC CARDIOMYOPATHY (ACM)

(71) Applicant: Beth Israel Deaconess Medical Center, Inc., Boston, MA (US)

(72) Inventor: Jeffrey E. Saffitz, Waban, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 1153 days.

(21) Appl. No.: 17/763,780

(22) PCT Filed: Sep. 25, 2020

(86) PCT No.: PCT/US2020/052811

§ 371 (c)(1),
(2) Date: Mar. 25, 2022

(87) PCT Pub. No.: WO2021/062217

PCT Pub. Date: Apr. 1, 2021

(65) Prior Publication Data

US 2022/0356240 A1 Nov. 10, 2022

Related U.S. Application Data

(60) Provisional application No. 62/906,502, filed on Sep. 26, 2019.

(51) Int. Cl.

| | |
|---|---|
| ***A61P 9/06*** | (2006.01) |
| ***A61K 39/395*** | (2006.01) |
| ***A61P 29/00*** | (2006.01) |
| *A61P 9/00* | (2006.01) |
| *C07K 14/545* | (2006.01) |
| *C07K 16/24* | (2006.01) |

(52) U.S. Cl.

CPC ............ *A61K 39/3955* (2013.01); *A61P 9/06* (2018.01); *A61P 29/00* (2018.01); *A61P 9/00* (2018.01); *C07K 14/545* (2013.01); *C07K 16/245* (2013.01); *C07K 2317/24* (2013.01)

(58) Field of Classification Search

CPC ................ C07K 14/545; C07K 16/245; A61K 39/3955; A61P 9/00; A61P 9/06

See application file for complete search history.

(56) References Cited

U.S. PATENT DOCUMENTS 7,446,175 B2 * 11/2008 Gram ........................ A61P 7/00 530/387.9
7,531,166 B2 * 5/2009 Masat ..................... A61P 27/02 530/388.1
9,085,621 B2 * 7/2015 Ke .......................... A61P 11/00
2009/0022729 A1 1/2009 Mackman et al.
2016/0375101 A1 12/2016 Oft
2017/0097363 A1 4/2017 Saffitz
2018/0030412 A1 2/2018 Walsh et al.
2018/0259539 A1 9/2018 Saffitz et al.

OTHER PUBLICATIONS

Campian et al., 2010. Eur J Nucl Med Mol Imaging. 37: 2079-2085.*
Benjamini et al., 1991. Immunology: A Short Course, 2nd edition, p. 40 only.*
Ferrara et al.(2015. mAbs. 7(1): 32-41).*
Amann et al., "Anti-inflammatory effects of aspirin and sodium salicylate," European Journal of Pharmacology, Jun. 28, 2002, 447(1):1-9.
Anzai et al., "The infarcted myocardium solicits GM-CSF for the detrimental oversupply of inflammatory leukocytes," Journal of Experimental Medicine, Nov. 6, 2017, 214(11):3293-310.
Asimaki et al., "A new diagnostic test for arrhythmogenic right ventricular cardiomyopathy," New England Journal of Medicine, Mar. 12, 2009, 360(11):1075-84.
Asimaki et al., "Altered desmosomal proteins in granulomatous myocarditis and potential pathogenic links to arrhythmogenic right ventricular cardiomyopathy," Circulation: Arrhythmia and Electrophysiology, Oct. 2011, 4(5):743-52.
Asimaki et al., "Characterizing the molecular pathology of arrhythmogenic cardiomyopathy in patient buccal mucosa cells," Circulation: Arrhythmia and Electrophysiology, Feb. 2016, 9(2):e003688, 13 pages.
Asimaki et al., "Identification of a new modulator of the intercalated disc in a zebrafish model of arrhythmogenic cardiomyopathy," Science Translational Medicine, Jun. 11, 2014, 6(240):240ra74, 32 pages.
Basso et al., "Arrhythmogenic right ventricular cardiomyopathy: dysplasia, dystrophy, or myocarditis?," Circulation, Sep. 1, 1996, 94(5):983-91.
Basso et al., "Pathophysiology of arrhythmogenic cardiomyopathy," Nature Reviews Cardiology, Apr. 2012, 9(4):223-33.
Bhattacharya et al., "High efficiency differentiation of human pluripotent stem cells to cardiomyocytes and characterization by flow cytometry," JoVE (Journal of Visualized Experiments), Sep. 23, 2014, (91):e52010, 12 pages.
Bhonsale et al., "Impact of genotype on clinical course in arrhythmogenic right ventricular dysplasia/cardiomyopathy-associated mutation carriers," European Heart Journal, Apr. 7, 2015, 36(14):847-55.
Bullock et al., "Phosphorylation of the cAMP response element binding protein CREB by cAMP-dependent protein kinase A and glycogen synthase kinase-3 alters DNA-binding affinity, conformation, and increases net charge," Biochemistry, Mar. 17, 1998, 37(11):3795-809.
Campbell et al., "Regulation of NF-kappaB function," Biochemical Society Symposium, Jan. 1, 2006, 73, 165-80.
Chelko et al., "Central role for GSK3β in the pathogenesis of arrhythmogenic cardiomyopathy," JCI Insight, Apr. 21, 2016, 1(5).
Coghlan et al., "Selective small molecule inhibitors of glycogen synthase kinase-3 modulate glycogen metabolism and gene transcription," Chemistry & Biology, Oct. 1, 2000, 7(10):793-803.
Corrado et al., "Arrhythmogenic right ventricular cardiomyopathy," New England Journal of Medicine, Jan. 5, 2017, 376(1):61-72.

(Continued)

*Primary Examiner* — Zachary C Howard
(74) *Attorney, Agent, or Firm* — Fish & Richardson P.C.

(57) ABSTRACT

Described herein are, inter alia, methods for treating arrhythmogenic cardiomyopathy (ACM) using anti-inflammatory agents that IL-1β.

7 Claims, 1 Drawing Sheet

(56) References Cited

OTHER PUBLICATIONS

Corrado et al., "Spectrum of clinicopathologic manifestations of arrhythmogenic right ventricular cardiomyopathy/dysplasia: a multicenter study," Journal of the American College of Cardiology, Nov. 15, 1997, 30(6):1512-20.
Dalal et al., "Arrhythmogenic right ventricular dysplasia: a United States experience," Circulation, Dec. 20, 2005, 112(25):3823-32.
De Jesus et al., "Anti-arrhythmic effects or interleukin-1 inhibition following myocardial infarction," Heart Rhythm, May 2017, 14(5): 727, 20 pages.
Dranoff et al., "Activities of granulocyte-macrophage colony-stimulating factor revealed by gene transfer and gene knockout studies," Stem Cells (Dayton, Ohio), Jan. 1, 1994, 12:173-82.
Dugo et al., "Glycogen synthase kinase 3β as a target for the therapy of shock and inflammation," Shock, Feb. 1, 2007, 27(2):113-23.
Fiol et al., "A secondary phosphorylation of CREB341 at Ser129 is required for the cAMP-mediated control of gene expression, A role for glycogen synthase kinase-3 in the control of gene expression," Journal of Biological Chemistry, Dec. 23, 1994, 269(51):32187-93.
Fontaine et al., "The arrhythmogenic right ventricle. Dysplasia versus cardiomyopathy," Heart and Vessels, Oct. 1995, 10(5):227-35.
Garcia-Gras et al., "Suppression of canonical Wnt/β-catenin signaling by nuclear plakoglobin recapitulates phenotype of arrhythmogenic right ventricular cardiomyopathy," The Journal of Clinical Investigation, Jul. 3, 2006, 116(7):2012-21.
Hamilton, "GM-CSF as a target in inflammatory/autoimmune disease: current evidence and future therapeutic potential," Expert Review of Clinical Immunology, Apr. 3, 2011, 11(4):457-65.
Harada et al., "Role of inflammation in atrial fibrillation pathophysiology and management," Circulation Journal, Feb. 25, 2015, 79(3):495-502.
Hariharan et al., "Arrhythmogenic right ventricular cardiomyopathy mutations alter shear response without changes in cell-cell adhesion," Cardiovascular Research, Nov. 1, 2014, 104(2):280-9.
Hayden et al., "Shared principles in NF-κB signaling," Cell. Feb. 8, 2008, 132(3):344-62.
Hoesel et al., "The complexity of NF-κB signaling in inflammation and cancer," Molecular Cancer, Dec. 2013, 12(1):1-5.
James et al., "Exercise increases age-related penetrance and arrhythmic risk in arrhythmogenic right ventricular dysplasia/cardiomyopathy-associated desmosomal mutation carriers," Journal of the American College of Cardiology, Oct. 1, 2013, 62(14):1290-7.
Kim et al., "Studying arrhythmogenic right ventricular dysplasia with patient-specific iPSCs, " Nature, Feb. 2013, 494(7435):105-10.
Klamer et al., "Using small molecule GSK3β inhibitors to treat inflammation," Current medicinal chemistry. Sep. 1, 2010;17(26):2873-81.
Kopp et al., "Inhibition of NF-κB by sodium salicylate and aspirin," Science, Aug. 12, 1994, 265(5174):956-9.
Lazzerini et al., "Systemic inflammation and arrhythmic risk: lessons from rheumatoid arthritis," European Heart Journal, Jun. 7, 2017, 38(22):1717-27.
Lombardi et al., "Nuclear plakoglobin is essential for differentiation of cardiac progenitor cells to adipocytes in arrhythmogenic right ventricular cardiomyopathy," Circulation Research, Dec. 9, 2011, 109(12):1342, 21 pages.
Lopez-Ayala et al., "Genetics of myocarditis in arrhythmogenic right ventricular dysplasia," Heart Rhythm, Apr. 1, 2015, 12(4):766-73.
Luo et al., "Involvement of MAPKs, NF-κB and p300 co-activator in IL-1β-induced cytosolic phospholipase A2 expression in canine tracheal smooth muscle cells," Toxicology and Applied Pharmacology, Nov. 1, 2008, 232(3):396-407.
MacRae et al., "Phase 2 study of A797, an oral, selective p38 mitogen-activated protein kinase inhibitor, in patients with Lamin A/C-related dilated cardiomyopathy," e-poster from European Society of Cardiology Congress, Aug 27-31, Rome, Italy, https://esc365.escardio.org/presentation/136910.
Marcus et al., "Diagnosis of arrhythmogenic right ventricular cardiomyopathy/dysplasia: proposed modification of the task force criteria," Circulation, Apr. 6, 2010, 121(13):1533-41.
Marcus et al., "Right ventricular dysplasia: a report of 24 adult cases," Circulation, Feb. 1982, 65(2):384-98.
Markham et al., "Corticosteroid treatment retards development of ventricular dysfunction in Duchenne muscular dystrophy," Neuromuscular Disorders, May 1, 2008, 18(5):365-70.
Martin et al., "Toll-like receptor-mediated cytokine production is differentially regulated by glycogen synthase kinase 3," Nature Immunology, Aug. 2005, 6(8):777-84.
McKoy et al., "Identification of a deletion in plakoglobin in arrhythmogenic right ventricular cardiomyopathy with palmoplantar keratoderma and woolly hair (Naxos disease)," The Lancet, Jun. 17, 2000, 355(9221):2119-24.
Mendell et al., "Randomized, double-blind six-month trial of prednisone in Duchenne's muscular dystrophy," New England Journal of Medicine, Jun. 15, 1989, 320(24):1592-7.
Miller et al., "Identification of known drugs that act as inhibitors of NF-κB signaling and their mechanism of action," Biochemical Pharmacology, May 1, 2010, 79(9):1272-80.
Misra et al., "Nuclear factor-κB protects the adult cardiac myocyte against ischemia-induced apoptosis in a murine model of acute myocardial infarction," Circulation, Dec. 23, 2003, 108(25):3075-8.
PCT International Preliminary Report on Patentability in International Appln. No. PCT/US2020/052811, dated Apr. 7, 2022, 6 pages.
PCT International Search Report and Written Opinion in International Appln. No. PCT/US2020/052811, dated Mar. 10, 2021, 7 pages.
Perkins et al., "Post-translational modifications regulating the activity and function of the nuclear factor kappa B pathway," Oncogene, Oct. 2006, 25(51):6717, 21 pages.
Ridker et al., "Anti-inflammatory therapy with cankinumab for atherosclerotic disease," New England Journal of Medicine, Sep. 21, 2017, 377(12):1119-31.
Rigato et al., "Compound and digenic heterozygosity predicts lifetime arrhythmic outcome and sudden cardiac death in desmosomal gene-related arrhythmogenic right ventricular cardiomyopathy," Circulation: Cardiovascular Genetics, Dec. 2013, 6(6):533-42.
Rojas et al., "Present understanding of the relationship between exercise and arrhythmogenic right ventricular dysplasia/cardiomyopathy," Trends in Cardiovascular Medicine, Apr. 1, 2015, 25(3):181-8.
Sakai et al., "p38 MAPK phosphorylation and NF-κ B activation in human crescentic glomerulonephritis," Nephrology Dialysis Transplantation, Jun. 1, 2002, 17(6):998-1004.
Sen-Chowdhry et al., "Arrhythmogenic cardiomyopathy: etiology, diagnosis, and treatment," Annual Review of Medicine, Feb. 18, 2010, 61:233-53.
Syed et al., "Murine echocardiography: a practical approach for phenotyping genetically manipulated and surgically modeled mice," Journal of the American Society of Echocardiography, Sep. 1, 2005, 18(9):982-90.
Takada et al., "Genetic deletion of glycogen synthase kinase-3β abrogates activation of IκB⊕ kinase, JNK, Akt, and p44/p42 MAPK but potentiates apoptosis induced by tumor necrosis factor," Journal of Biological Chemistry, Sep. 17, 2004, 279(38):39541-54.
Te Riele et al., "Arrhythmogenic right ventricular cardiomyopathy (ARVC): cardiovascular magnetic resonance update," Journal of Cardiovascular Magnetic Resonance, Dec. 2014, 16(1):1-5.
Thiene et al., "Right ventricular cardiomyopathy and sudden death in young people," New England Journal of Medicine, Jan. 21, 1988, 318(3):129-33.
Ushach et al., "Biological role of granulocyte macrophage colony-stimulating factor (GM-CSF) and macrophage colony-stimulating factor (M-CSF) on cells of the myeloid lineage, " Journal of Leukocyte Biology, Sep. 2016, 100(3):481-9.
Vercammen et al., "Prolonged exposure to IL-1β and IFNγ induces necrosis of L929 tumor cells via a p38MAPK/NF-κB/NO-dependent mechanism," Oncogene, Jun. 2008, 27(27):3780-8.

(56) References Cited

OTHER PUBLICATIONS

Wicks et al., "Targeting GM-CSF in inflammatory diseases," Nature Reviews Rheumatology, Jan. 2016, 12(1):37-48.
Yuan et al., "Reversal of obesity-and diet-induced insulin resistance with salicylates or targeted disruption of Ikkβ," Science, Aug. 31, 2001, 293(5535):1673-7.
Zhan et al., "Wnt signaling in cancer," Oncogene, Mar. 2017, 36(11):1461-73.

* cited by examiner

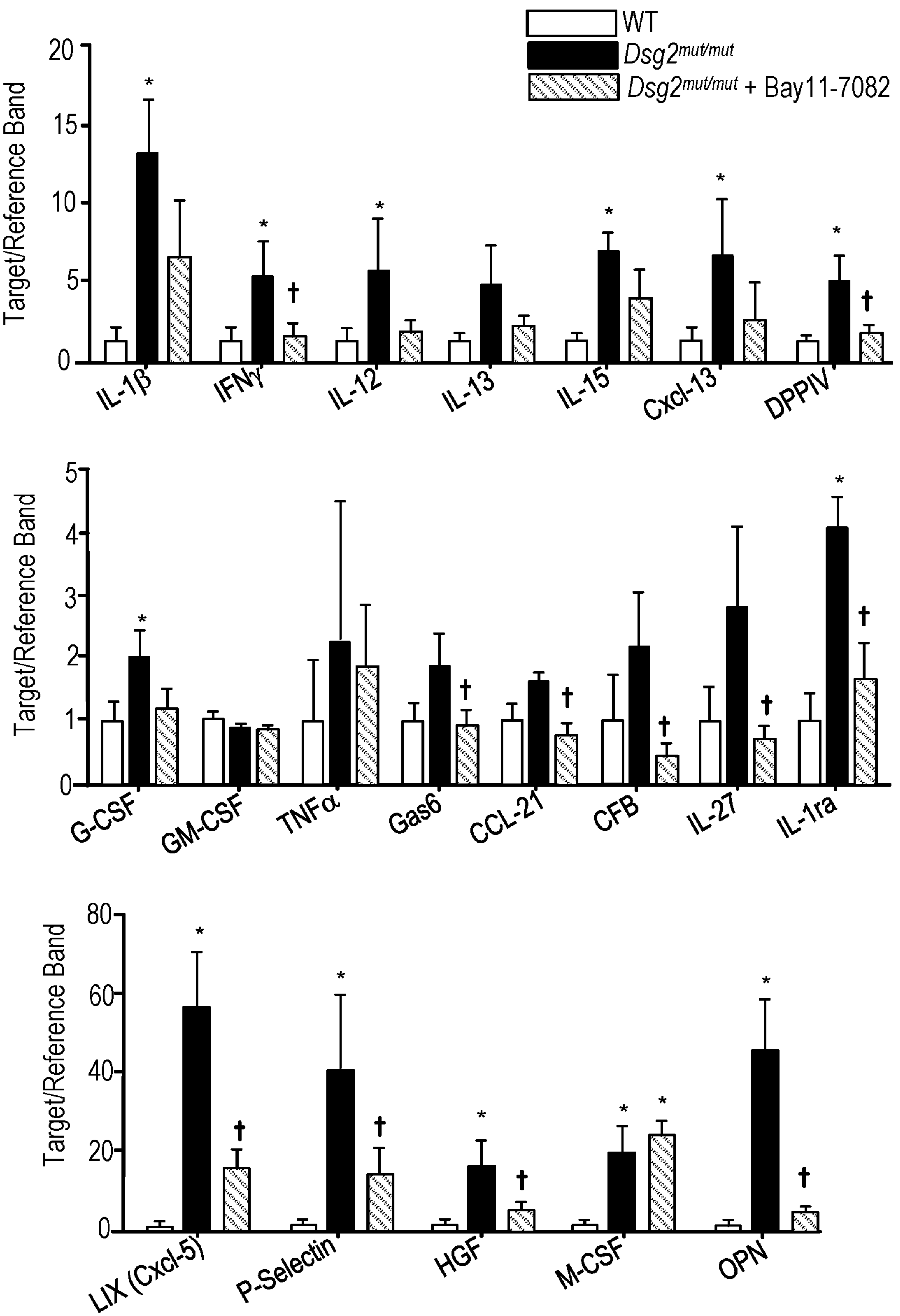
WT
Dsg2mut/mut
Dsg2mut/mut + Bay11-7082
Target/Reference Band
20
15
10
5
0
IL-1β
IFNγ
IL-12
IL-13
IL-15
Cxcl-13
DPPIV
5
4
3
2
1
0
G-CSF
GM-CSF
TNFα
Gas6
CCL-21
CFB
IL-27
IL-1ra
80
60
40
20
0
LIX (Cxcl-5)
P-Selectin
HGF
M-CSF
OPN

ANTI-IL-1β ANTIBODY THERAPY IN ARRHYTHMOGENIC CARDIOMYOPATHY (ACM)

CLAIM OF PRIORITY

This application claims the benefit of U.S. Patent Application Ser. No. 62/906,502, filed on Sep. 26, 2019.

TECHNICAL FIELD

Described herein are, inter alfa, methods for treating arrhythmogenic cardiomyopathy (ACM) using anti-inflammatory agents that target IL-1β.

BACKGROUND

Arrhythmogenic cardiomyopathy (ACM), also known as arrhythmogenic right ventricular cardiomyopathy in particular (ARVC), is associated with a high frequency of arrhythmias and sudden cardiac death (Marcus et al., Circulation 1982; 65:384-98; Thiene et al., N Engl J Med 1988; 318: 129-33; Dalal et al., Circulation 2005; 112:3823-32), ACM is a familial non-ischemic heart muscle disease that causes sudden death in the young and especially in athletes.[1-3] Heightened risk in athletes underscores increasing awareness that intense exercise accelerates disease penetrance, and increases arrhythmic risk and adverse cardiac events in subjects who harbor ACM disease alleles.[4,5] Currently, the only effective treatment is an Implantable Cardioverter Defibrillator (ICD). Mutations in genes encoding desmosomal proteins (including desmoplakin, plakoglobin, plakophilin 2, desmocollin 2, and desmoglein 2) have been identified in approximately 60% of patients with ARVC (te Riele et al., J Cardiovasc Magn Reson. 2014; 16:50).

SUMMARY

As shown herein, an innate immune response in cardiac myocytes drives the ACM disease phenotype.

Thus, provided herein are methods for treating a subject with arrhythmogenic cardiomyopathy (ACM). The methods include identifying a subject as having or at risk of developing ACM; and administering to the subject a therapeutically effective amount of an inhibitor of IL-1 receptor.

In addition to the methods, also provided herein are pharmaceutical compositions including an inhibitor of IL-1β, for use in a method of treating a subject with arrhythmogenic cardiomyopathy (ACM), wherein the subject has or is at risk of developing ACM.

In some embodiments, the methods or compositions, as described above, may further include one or more of recommending or advising the subject to avoid strenuous or intense physical activity or exercise; recommending or prescribing or administering one or more Singh Vaughan Williams class II antiarryhthmics (beta blockers) such as propranolol, esmolol, timolol, metoprolol, or atenolol; recommending or prescribing or administering one or more class III anti-arrhythmics (K-channel blockers) such as amiodarone, sotalol, ibutilide, dofetilide, dronedarone or E-4031; recommending or performing cardiac ablation; or recommending or implanting an implantable cardiac defibrillator (ICD).

In some embodiments, the inhibitor of the IL-1 receptor is an IL-1R antagonist, an IL-1R decoy, or an anti-IL-1β antibody, or preferably a chimeric, humanized, or fully human anti-IL-1β antibody.

In some embodiments, the inhibitor of the IL-1 receptor is selected from the group consisting of anakinra, canakinumab, rilonacept, APX002, CDP48, immunereszumab, LY2189102, MEDI8968, and XOMA052.

In some embodiments, the inhibitor of the IL-1 receptor is an inhibitor of IL-1β.

In some embodiments, the inhibitor of IL-1β is an anti-IL-1β antibody.

In some embodiments, the anti-IL-1β antibody is a chimeric, humanized, or fully human antibody.

In some embodiments, the inhibitor is a small molecule or microRNA inhibitor that inhibits IL-1β-mediated pro-inflammatory activity.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and FIGURES, and from the claims.

DESCRIPTION OF DRAWINGS

FIG. 1 shows cytokine expression in the hearts of Dsg2$^{mut/mut}$ mice and its attenuation by Bay 11-7082. Quantitative data (mean±SEM; n=5) for expression of selected cytokines in hearts of vehicle-treated wildtype (WT) mice, Dsg2$^{mut/mut}$ mice and Dsg2$^{mut/mut}$ mice treated with Bay 11-7082. * $P<0.05$ compared to WT; †$P<0.05$ for treated vs. untreated Dsg2$^{mut/mut}$ mice.

DETAILED DESCRIPTION

Inflammation has been recognized as a feature of ACM for as long as the disease has been known.[8] First described by autopsy pathologists,[9] inflammatory infiltrates occur in the hearts of 60 to 88% of ACM patients, and are especially common in ACM patients who died suddenly.[9,10] It has been suggested that a histologic picture reminiscent of acute myocarditis may reflect an active phase of ACM associated with accelerated disease progresssion,[11] but the presence of inflammatory cells in the myocardium in ACM is only part of the story. ACM patients have elevated circulating levels of pro-inflammatory cytokines, and cardiac myocytes themselves produce potent cytokines in ACM.[12] Thus, inflammation in ACM is complex. It involves infiltrating inflammatory cells and activation of an immune response in cardiac myocytes, one or both of which may contribute to disease expression. However, this question has never been rigorously investigated. Immune activation occurs in many heart diseases (ischemia/reperfusion, pressure/volume overload, infections, autoimmunity) but its contribution to tissue injury varies greatly in specific settings. There is a large literature on the potential role of inflammatory cytokines in heart failure, but relatively little work has been done on this question in the cardiomyopathies. Whereas corticosteroid use in Duchenne muscular dystrophy is associated with improved cardiac function and reduced fibrosis,[13,14] the role of inflammation as a driver of myocardial injury in the non-ischemic cardiomyopathies has not been studied in detail.

Both components of the immune response in ACM likely contribute to disease pathogenesis. The most conspicuous component is infiltration of the myocardium by "professional" cells of the adaptive immune response—lymphocytes and macrophages. Indeed, inflammatory cells can be so abundant in the hearts of ACM patients that the disease may be misdiagnosed as myocarditis.[52] However, it has never been clear if inflammatory cells accumulate in the heart in ACM only as a reparative response to myocardial damage or if such cells actually promote arrhythmias and/or myocyte injury mediated by immune mechanisms. The second component involves activation of an innate immune response in cardiac myocytes in ACM. How this occurs is unclear although it is known that activation of GSK3β promotes inflammation through NFκB signaling.[21-24] We previously showed that cardiac myocytes that express variants in 3 different desmosomal genes known to cause ACM in patients produce and secrete large amounts of diverse chemical mediators of the immune response. Many of these are powerful chemoattractant molecules that likely play an important role in mobilizing bone marrow-derived inflammatory cells to the heart. Cardiac myocytes in ACM also produce powerful pro-inflammatory mediators such as IL-1β and TNFα, both of which are considered primordial cytokines of the innate immune response. This suggests that activation of immune signaling within cardiac myocytes may play an important role in driving the key clinical features of the disease. It also raises the interesting possibility that cytokines made and secreted by cardiac myocytes act in an autocrine fashion to alter ion channel function and promote arrhythmias in ACM. If so, this would add to the traditional view of the role of inflammation in arrhythmogenesis which holds that cardiac ion channel dysfunction is mediated by cytokines produced by lymphocytes and macrophages that infiltrate the heart in myocarditis or other inflammatory heart diseases.[53]

Glycogen synthase kinase-3β (GSK3β) plays a central role in the pathogenesis of ACM.[6] A small molecule, SB216763, annotated as an inhibitor of GSK3β,[7] has a remarkable ability to prevent and/or reverse the full ACM disease phenotype (arrhythmias, exercise-induced sudden death, ventricular myocyte injury and apoptosis, inflammation, and contractile dysfunction) in multiple in vitro and in vivo models of ACM, and in human iPSC-cardiac myocytes derived from ACM patients.[6,7] See also US2017/0097363. Thus the clinically important features of the disease phenotype—arrhythmias and myocardial damage—arise via a common disease mechanism that can be blocked by a single small molecule (SB216763).

GSK3β acts on and with a large and varied number of other signaling molecules; in inflammation crosstalk between pathways complicates the picture even further. See, e.g., Hoesel and Schmid, Mol Cancer. 2013; 12:86. ACM disease alleles activate NFκB signaling in cardiac myocytes. Surprisingly, inhibition of this signaling system is as effective as SB216763 in preventing the full ACM disease phenotype. This provides new evidence that ACM is an inflammatory disease.

One of the more striking observations was the production and secretion of diverse pro-inflammatory cytokines and chemoattractants by ACM patient-derived cardiac myocytes grown under basal conditions in vitro. In previous studies of such cell lines,[49] it was necessary to use a combination of provocative stimuli (dexamethasone, 3-isobutyl-1-methylxanthine, rosiglitazone and indomethacin) to induce metabolic changes seen in patients with ACM. By contrast, we showed that expression of a common variant in PKP2 is sufficient to induce marked expression of immune mediators by human cardiac myocytes under basal conditions and in the absence of inflammatory cells. This observation, combined with results from in vitro and in vivo experimental models (which involved 2 different desmosomal mutations) suggests that activation of an innate immune response in cardiac myocytes occurs as a cell autonomous process in response to multiple ACM disease alleles independent of the actions of professional inflammatory cells.

Although our previous results did not prove that cytokines are responsible for causing myocardial damage and arrhythmias in ACM, there was a clear correlation between activation of an immune response and expression of the disease phenotype. Expression levels of two cytokines in particular, LIX (CXCL5) and osteopontin (OPN), were found to correlate with ejection fraction in $Dsg2^{mut/mut}$ mice. LIX was increased by >50-fold in $Dsg2^{mut/mut}$ mice and its level was markedly reduced in ACM mice treated with Bay 11-7082. Production of LIX is stimulated by IL-1β and TNFα. It promotes chemotaxis of neutrophils and also plays a role in fibrosis. OPN expression was increased by >40-fold in $Dsg2^{mut/mut}$ mice and it too was reduced by Bay 11-7082. OPN regulates cell adhesion and survival. It also acts as a Th1 cytokine and participates in cell-mediated immune responses. In turn, expression of LIX and OPN was correlated with expression of other mediators including CCL21 (a T-cell and dendritic cell attractant), complement factor D (required for activation of the alternative pathway), DPP-IV (a dipeptidyl peptidase involved in immune regulation and apoptosis), GAS6 (which plays a role in fibrosis), IFNγ, IL-1Ra and IL-27 (which induces T-cell differentiation and upregulates IL-10 which itself was increased in ACM mice). These observations suggest that networks of immune mediators, likely derived from both cardiac myocytes and infiltrating inflammatory cells, interact in a complex fashion to promote the ACM disease phenotype.

Our results raised the possibility that targeting immune signaling could be an effective mechanism-based therapy in ACM. This notion is in keeping with recent insights into the role of immune activation in coronary artery disease and heart failure. Numerous drugs that block NFκB signaling are approved by the US Food and Drug Administration, mainly for treating cancer.[54] In the CANTOS trial, a monoclonal antibody against IL-1β significantly reduced major adverse cardiac events in patients with coronary artery disease.[36] In addition, long-term treatment with the anti-IL-1β antibody was not associated with significant infectious complications related to immunosuppression.[36] IL-1β is a primordial cytokine of the innate immune response. It plays a major role in activating NFκB pathways. Accordingly, the fact that IL-10 expression was increased by ~13-fold in in $Dsg2^{mut/mut}$ mice suggests it may be a major driver of immune signaling in ACM. This provided the rationale for studies described here involving anti-IL1β as a therapeutic strategy in ACM. Finally, strenuous exercise is known to accelerate disease penetrance and increase arrhythmic risk in ACM patients.[4,5] It remains to be determined if exercise intensifies the immune response in ACM and, if so, whether anti-inflammatory therapy might mitigate its adverse effects.

Methods of Treatment

Accordingly, in some embodiments, the methods described herein include administering a treatment comprising an inhibitor of IL-1β to a subject identified as having ACM or being at risk for ACM (i.e., based on family history or the presence of genetic mutations associated with ACM). A subject can be identified as having ACM (diagnosed with ACM) based on methods known in the art, and/or using the methods described in US2017/0097363. A diagnosis usually rests on fulfilling a set of clinical criteria; see, e.g., Marcus et al., Circulation, 2010; 121:1533-1541.

As used herein, the term "patient" or "subject" refers to members of the animal kingdom including but not limited to human beings and "mammal" refers to all mammals, including, but not limited to human beings.

As used herein, the "treatment" or "treating" ACM means administration to a patient by any suitable dosage regimen, procedure and/or administration route of a composition, device or structure with the object of achieving a desirable clinical/medical end-point, including but not limited to, eliminating/reducing/preventing inflammation.

The methods can also include recommending or advising the subject to avoid strenuous or intense physical activity or exercise; recommending or prescribing or administering one or more Singh Vaughan Williams class II antiarryhthmics (beta blockers) such as propranolol, esmolol, timolol, metoprolol, or atenolol; recommending or prescribing or administering one or more class III anti-arrhythmics (K-channel blockers) such as amiodarone, sotalol, ibutilide, dofetilide, dronedarone or E-4031; recommending or performing cardiac ablation; or recommending or implanting an implantable cardiac defibrillator (ICD).

IL-1β Inhibitors

Interleukin-1 (IL-1) is the prototypical inflammatory cytokine: two distinct ligands (IL-1α and IL-1β) bind the IL-1 type 1 receptor (IL-1R1) and induce a myriad of secondary inflammatory mediators, including prostaglandins, cytokines, and chemokines. IL-1α is constitutively present in endothelial and epithelial cells, whereas IL-1β is inducible in myeloid cells and released following cleavage by caspase-1. Therefore, in some embodiments, the IL-1β inhibitor is an IL-1R antagonist, an IL-1R decoy (a decoy receptor is a receptor that is able to recognize and bind specific growth factors or cytokines efficiently, but is not structurally able to signal or activate the intended receptor complex), an anti-IL-1β antibody (i.e., a neutralizing antibody), a humanized anti-IL-1β antibody.

Examples of IL-1β inhibitors include but are not limited to anakinra (the recombinant form of the naturally occurring IL-1 receptor antagonist (IL-1Ra); IL-1Ra prevents the binding of IL-1α as well as IL-1β to IL-1R1), canakinumab (recombinant, human anti-human-IL-1β monoclonal antibody; available from Novartis), rilonacept (a dimeric fusion protein consisting of portions of IL-1R and the IL-1R accessory protein linked to the Fc portion of immunoglobulin G1). Other examples of IL-1β inhibitors include but are not limited to APX002, CDP48, immunereszumab, LY2189102, MEDI8968, and XOMA052.

In some embodiments described herein, the IL-1β inhibitor is a small molecule or microRNA inhibitor that inhibits IL-1β-mediated pro-inflammatory activity.

As used herein, an "IL-1β inhibitory compound" or "IL-1β inhibitor" or "inhibitor of IL-1β refers to a compound" or agent capable of specifically inhibiting or specifically preventing activation of cellular receptors to IL-1β and consequent downstream effects of IL-1β signaling.

Also provided herein are pharmaceutical compositions comprising an "IL-1β inhibitory compound" or "IL-1β inhibitor" or "inhibitor of IL-1β." The pharmaceutical composition, wherein the IL-1β inhibitor is an IL-1β inhibitor antibody or antigen-binding fragment thereof that binds to IL-1β and reduces IL-1β binding to its receptor(s).

DSG2

As used herein the term "desmoglein-2" or "DSG2" has its general meaning in the art and refers to a member of the desmoglein protein subfamily. Exemplary sequences for human desmoglein 2 is available in GenBank at Acc no. NM_001943.5 (nucleic acid (and NP_001934.2 (desmoglein-2 preproprotein). Desmoglein-2 is highly expressed in epithelial cells and cardiomyocytes. Desmoglein-2 is localized to desmosome structures at regions of cell-cell contact and functions to structurally adhere adjacent cells together. In cardiac muscle, these regions are specialized regions known as intercalated discs. Mutations in desmoglein-2 have been associated with arrhythmogenic right ventricular cardiomyopathy and familial dilated cardiomyopathy.

In some embodiments, the methods of treatment described herein can be used in a subject who has ACM, wherein the method comprises a first step for determining whether the subject suffering from ACM has a DSG2 deficiency. For instance by determining if the subject has a mutation in the DSG2 gene. Or, by measuring the level/amount of DSG2 protein. Detection of a mutation or measuring of protein levels may be conducted by any appropriate and routine method known to one of ordinary skill in the art.

As used herein, the term "DSG2 deficiency" denotes that the cells of the subject or a part thereof have a DSG2 dysfunction, a low or a null expression of desmoglein-2. Said deficiency may typically result from a mutation in so that the pre-mRNA is degraded through the NMD (nonsense mediated decay) system. Said deficiency may also typically result from a mutation so that the protein is misfolded and degraded through the proteasome. Said deficiency may also result from a loss of function mutation leading to a dysfunction of the protein. Said deficiency may also result from an epigenetic control of gene expression (e.g. methylation) so that the gene is less expressed in the cells of the subject. Said deficiency may also result from a repression of the DSG2 gene induce by a particular signaling pathway.

General Definitions

Antibody

The term "antibody" as used herein refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments the antibody has effector function and can fix complement. In some embodiments, the antibody has reduced or no ability to bind an Fc receptor. For example, the antibody can be an isotype or subtype, fragment or other mutant, which does not support binding to an Fc receptor, e.g., it has a mutagenized or deleted Fc receptor binding region. Methods for making antibodies and fragments thereof are known in the art, see, e.g., Harlow et. al., editors, Antibodies: A Laboratory Manual (1988); Goding, Monoclonal Antibodies: Principles and Practice, (N.Y. Academic Press 1983); Howard and Kaser, Making and Using Antibodies: A Practical Handbook (CRC Press; 1st edition, Dec. 13, 2006); Kontermann and Dübel, Antibody Engineering Volume 1 (Springer Protocols) (Springer; 2nd ed., May 21, 2010); Lo, Antibody Engineering: Methods and Protocols (Methods in Molecular Biology) (Humana Press; Nov. 10, 2010); and Dübel, Handbook of Therapeutic Antibodies: Technologies, Emerging Developments and Approved Therapeutics, (Wiley-VCH; 1 edition Sep. 7, 2010).

Pharmaceutical Compositions

Pharmaceutical compositions comprising an agent capable of achieving the desired endpoint may be prepared by any method known in the art of pharmacy, for example by bringing into association the active ingredient with the carrier(s) or excipient(s). As used herein, "carrier" or "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it may be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the active agent. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art.

Additionally, compositions described herein may be in variety of forms. The preferred form depends on the intended mode of administration and therapeutic application, which will in turn dictate the types of carriers/excipients. Suitable forms include, but are not limited to, liquid, semi-solid and solid dosage forms.

Pharmaceutical formulations adapted for oral administration may be presented, for example and without limitation, as discrete units such as capsules or tablets; powders or granules; solutions or suspensions in aqueous or non-aqueous liquids; edible foams or whips; or oil-in-water liquid emulsions or water-in-oil liquid emulsions. In certain embodiments, the active agent may be contained in a formulation such that it is suitable for oral administration, for example, by combining the active agent with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Pharmaceutical formulations adapted for transdermal administration may be presented, for example and without limitation, as discrete patches intended to remain in intimate contact with the epidermis of the recipient for a prolonged period of time or electrodes for iontophoretic delivery.

Pharmaceutical formulations adapted for topical administration may be formulated, for example and without limitation, as ointments, creams, suspensions, lotions, powders, solutions, pastes, gels, sprays, aerosols or oils.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient. Pharmaceutical formulations adapted for administration by inhalation include, without limitation, fine particle dusts or mists which may be generated by means of various types of metered dose pressurized aerosols, nebulizers or insufflators.

Pharmaceutical formulations adapted for parenteral administration include aqueous and non-aqueous sterile injection solutions which may contain, for example and without limitation, anti-oxidants, buffers, bacteriostats, lipids, liposomes, emulsifiers, also suspending agents and rheology modifiers. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Therapeutic compositions typically must be sterile and stable under the conditions of manufacture and storage. For example, sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, typical methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

Compositions comprising the agents of the present invention can be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

A "therapeutically effective amount" refers to an amount effective, at dosages and for periods of time necessary, to achieve the desired therapeutic result. An "amount effective"

for treatment of a condition is an amount of an active agent or dosage form, such as the coacervate composition described herein, effective to achieve a determinable end-point. The "amount effective" is preferably safe—at least to the extent the benefits of treatment outweighs the detriments and/or the detriments are acceptable to one of ordinary skill and/or to an appropriate regulatory agency, such as the U.S. Food and Drug Administration. A therapeutically effective amount may vary according to factors such as the disease state, age, sex, and weight of the individual, and the ability of the active agent to elicit a desired response in the individual. A therapeutically effective amount is also one in which any toxic or detrimental effects of the active agent are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount may be less than the therapeutically effective amount.

Dosage regimens may be adjusted to provide the optimum desired response (e.g., a therapeutic or prophylactic response). For example, a single bolus may be administered, several divided doses may be administered over time, or the composition may be administered continuously or in a pulsed fashion with doses or partial doses being administered at regular intervals, for example, ever 10, 15, 20, 30, 45, 60, 90, or 120 minutes, every 2 through 12 hours daily, or every other day, etc. be proportionally reduced or increased as indicated by the exigencies of the therapeutic situation. In some instances, it may be especially advantageous to formulate parenteral compositions in dosage unit form for ease of administration and uniformity of dosage. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

EXAMPLES

The invention is further described in the following examples, which do not limit the scope of the invention described in the claims.

Example 1

Cytokines are Produced by Cardiac Myocytes and Infiltrating Inflammatory Cells in ACM To characterize production of chemical mediators of the immune response in ACM, we used arrays to measure 111 different cytokines in the hearts of $Dsg2^{mut/mut}$ mice and compared the amounts to those measured in the hearts of WT mice and $Dsg2^{mut/mut}$ mice treated with Bay 11-7082. We observed substantial expression of multiple cytokines in the hearts of $Dsg2^{mut/mut}$ mice. FIG. 1 shows data for selected cytokines (the complete data set is included in Table 1). Powerful inflammatory mediators were expressed in $Dsg2^{mut/mut}$ hearts including IL-1β (up by ~13-fold compared to WT hearts), IFNγ (~5-fold), IL-12 (~6-fold) and TNFα (~2-fold). Similarly, various chemotactic molecules were greatly increased in $Dsg2^{mut/mut}$ hearts compared to WT hearts, including the B-cell chemoattractant CXCL13 (up by ~6-fold), M-CSF (~20-fold), and the neutrophil chemoattractant LIX (CXCL5; ~60-fold). And, expression of various pleomorphic molecules with multiple actions was also greatly increased including HGF (~15-fold) and P-selectin (~40-fold). Finally, there were increases in some molecules that fulfill anti-inflammatory roles such as IL-1Ra (up by ~4-fold). In most, but not all, cases increased expression of these molecules in $Dsg2^{mut/mut}$ hearts was blunted or fully normalized by treatment with Bay 11-7082 (FIG. 1).

TABLE 2

Cytokine expression levels for in vivo studies in mice.

| Target | $Dsg2^{mut/mut}$ vs WT | $Dsg2^{mut/mut}$ (Bay11-7082) vs WT | $Dsg2^{mut/mut}$ (Bay11-7082) vs $Dsg2^{mut/mut}$ |
|---|---|---|---|
| Adiponectin | <1 | <1 | <1 |
| Amphiregulin | <1 | <1 | <1 |
| Angiopoietin-1 | <1 | <1 | <1 |
| Angiopoietin-2 | <1 | <1 | 1-2 |
| Angiopoietin-like 3 | <1 | <1 | <1 |
| BAFF/BLyS/TNFSF13B | <1 | <1 | <1 |
| C1qR1/CD93 | 1-2 | <1 | <1 |
| CCL2/JE/MCP-1 | <1 | <1 | <1 |
| CCL3/CCL4/MIP-1a/B | <1 | <1 | <1 |
| CCL5/RANTES | <1 | <1 | <1 |
| CCL6/C10 | <1 | <1 | <1 |
| Eotaxin (CCL11) | <1 | <1 | <1 |
| MCP-5 (CCL12) | <1 | <1 | <1 |
| CCL17/TARC | <1 | <1 | <1 |
| CCL19/MIP-3B | <1 | <1 | <1 |
| CCL20/MIP-3a | 1-2 | <1 | <1 |
| CCL21/6Ckine | 1-2 | <1 | <1 |
| CCL22/MDC | <1 | <1 | <1 |
| CD14 | <1 | <1 | 1-2 |
| CD40/TNFRSF5 | <1 | <1 | <1 |
| CD160 | 1-2 | <1 | <1 |
| Chemerin | <1 | <1 | <1 |
| Chitinase 3-like 1 | <1 | <1 | <1 |
| Coagulation Factor III/ Tissue Factor | <1 | <1 | <1 |
| Complement Component C5/C5a | 1-2 | <1 | <1 |
| Complement Factor D | 2-4 | <1 | <1 |
| C-Reactive Protein/CRP | 1-2 | <1 | <1 |
| CX3CL1/Fractalkine | <1 | <1 | <1 |
| KC (CXCL1) | <1 | <1 | <1 |
| MIP-2 (CXCL2) | <1 | <1 | <1 |
| CXCL9/MIG | 1-2 | <1 | <1 |
| IP-10 (CXL10/CRG-2) | 1-2 | <1 | <1 |
| I-TAC (CXCL11) | 1-2 | <1 | <1 |
| CXCL13/BLC/BCA-1 | 6-10 | 2-4 | <1 |
| CXCL16 | 1-2 | <1 | <1 |
| Cystatin C | 1-2 | <1 | <1 |
| DKK-1 | 2-4 | <1 | <1 |
| DPPIV/CD26 | 4-6 | 1-2 | <1 |
| EGF | 2-4 | 1-2 | <1 |
| Endoglin/CD105 | <1 | <1 | <1 |
| Endostatin | 1-2 | <1 | <1 |
| Fetuin A/AHSG | 1-2 | <1 | <1 |
| FGF acidic | 1-2 | <1 | <1 |
| FGF-21 | 1-2 | <1 | <1 |
| FLt-3 Ligand | 2-4 | <1 | <1 |
| Gas 6 | 1-2 | <1 | <1 |
| G-CSF | 2-4 | 1-2 | <1 |
| GDF-15 | 1-2 | <1 | <1 |
| GM-CSF | <1 | <1 | <1 |
| HGF | >10 | 4-6 | <1 |
| sICAM-1 (CD54) | 1-2 | 1-2 | <1 |
| IFN-y | 4-6 | 1-2 | <1 |
| IGFBP-1 | 2-4 | 1-2 | <1 |
| IGFBP-2 | 2-4 | <1 | <1 |
| IGFBP-3 | 1-2 | <1 | <1 |
| IGFBP-5 | 1-2 | <1 | <1 |
| IGFBP-6 | 2-4 | <1 | <1 |
| IL-1a (IL-1F1) | 2-4 | <1 | <1 |
| IL-1β (IL-1F2) | >10 | 6-10 | <1 |
| IL-1ra (IL-1F3) | 4-6 | 1-2 | <1 |
| IL-2 | <1 | <1 | <1 |
| IL-3 | <1 | <1 | <1 |

TABLE 2-continued

Cytokine expression levels for in vivo studies in mice.

| Target | $Dsg2^{mut/mut}$ vs WT | $Dsg2^{mut/mut}$ (Bay11-7082) vs WT | $Dsg2^{mut/mut}$ (Bay11-7082) vs $Dsg2^{mut/mut}$ |
|---|---|---|---|
| IL-4 | 1-2 | <1 | <1 |
| IL-5 | <1 | <1 | <1 |
| IL-6 | <1 | <1 | <1 |
| IL-7 | 1-2 | <1 | <1 |
| IL-10 | 1-2 | <1 | <1 |
| IL-11 | 1-2 | <1 | <1 |
| IL-12 p40 | 4-6 | 1-2 | <1 |
| IL-13 | 4-6 | 1-2 | <1 |
| IL-15 | 6-10 | 2-4 | <1 |
| IL-17a | <1 | <1 | <1 |
| IL-22 | <1 | <1 | <1 |
| IL-23 | <1 | <1 | <1 |
| IL-27 p28 | 2-4 | <1 | <1 |
| IL-28A/B | 1-2 | 1-2 | <1 |
| IL-33 | 2-4 | 2-4 | <1 |
| LDL R | <1 | 1-2 | 1-2 |
| Leptin | 2-4 | 1-2 | <1 |
| LIF | 1-2 | <1 | <1 |
| Lipocalin-2/NGAL | <1 | <1 | <1 |
| LIX | >20 | >10 | <1 |
| M-CSF | >10 | >20 | 1-2 |
| MMP-2 | 4-6 | 4-6 | 1-2 |
| MMP-3 | <1 | <1 | 1-2 |
| MMP-9 | <1 | <1 | <1 |
| Myeloperoxidase | 4-6 | 2-4 | <1 |
| Osteopontin (OPN) | >20 | 4-6 | <1 |
| Osteoprotegerin/ TNFRSF11B | <1 | <1 | <1 |
| PD-EGF/Thymidine phosphorylase | <1 | <1 | <1 |
| PDGF-BB | 2-4 | 1-2 | <1 |
| Pentraxin 2/SAP | 4-6 | 1-2 | <1 |
| Pentraxin 3/TSG-14 | <1 | <1 | <1 |
| Periostin/OSF-2 | <1 | <1 | <1 |
| Pref-1/DLK-1/FA1 | 6-10 | 6-10 | <1 |
| Proliferin | 6-10 | 6-10 | <1 |
| Proprotein Convertase 9/PCSK9 | <1 | <1 | 1-2 |
| RAGE | <1 | <1 | <1 |
| RBP4 | 1-2 | 1-2 | <1 |
| Reg3G | 6-10 | 6-10 | <1 |
| Resistin | 2-4 | 2-4 | <1 |
| E-Selectin/CD62E | <1 | <1 | <1 |
| P-Selectin/CD62P | >20 | >10 | <1 |
| Serpin E1/PAI-1 | >10 | 6-10 | <1 |
| Serpin F1/PEDF | <1 | <1 | <1 |
| Thrombopoeitin | <1 | <1 | 1-2 |
| TIM-1/KIM-1/HAVCR | <1 | <1 | 1-2 |
| TNF-α | 2-4 | 1-2 | <1 |
| VCAM-1/CD106 | 4-6 | 6-10 | 1-2 |
| VEGF | <1 | <1 | 1-2 |
| WISP-1/CCN4 | <1 | <1 | <1 |

From the cytokine assays shown in FIG. 1, expression of IL-1β and TNFα in the hearts of $Dsg2^{mut/mut}$ mice suggests a role for monocyte/macrophages and expression of IFNγ suggests a role for T-cells. These observations indicated that inflammation in ACM involves activation of an innate immune response in cardiac myocytes driven, at least in part, by NFκB signaling.

REFERENCES

1. Sen-Chowdhry S, Morgan R D, Chambers J C, McKenna W J. Arrhythmogenic cardiomyopathy: etiology, diagnosis, and treatment. Annu Rev Med 2010; 61:233-53.
2. Basso C, Bauce B, Corrado D, Thiene G. Pathophysiology of arrhythmogenic cardiomyopathy. Nat Rev Cardiol 2012; 9:223-33.
3. Corrado D, Link M, Calkins H. Arrhythmogenic right ventricular cardiomyopathy. New Eng J Med, 2017; 376: 61-72.
4. James, C A, Bhonsale A, Tichnell C, Murray D. Russell S D, Tandri H, Tedford R J, Judge D P, Calkins H. Exercise increases age-related penetrance and arrhythmic risk in arrhythmogenic right ventricular dysplasia/cardiomyopathy-associated desmosomal mutation carriers. J Am Coll Cardiol 2013; 62:1290-1297.
5. Rojas A, Calkins H. Present understanding of the relationship between exercise and arrhythmogenic right ventricular dysplasia/cardiomyopathy. Trends Cardiovasc Med 2015; 25:181-188.
6. Chelko S P, Asimaki A, Andersen P, Bedja D, Amat-Alarcon N, DeMazumder D, Jasti R, MacRae C A, Leber R, Kleber A G, Saffitz J E, Judge D P. Central role for GSK3β in the pathogenesis of arrhythmogenic cardiomyopathy. JCI Insight 2016:1(5). pii: e85923.
7. Asimaki A, Kapoor S, Plovie E, Karin Arndt A, Adams E, Liu Z, James C A, Judge D P, Calkins H, Churko J, Wu J C, MacRae C A, Kléber A G, Saffitz J E. Identification of a new modulator of the intercalated disc in a zebrafish model of arrhythmogenic cardiomyopathy. Sci Transl Med 2014; 6:240ra74.
8. Marcus F I, Fontaine G H, Guiraudon G, Frank R, Laurenceau J L, Malergue C, Grogogeat Y. Right ventricular dysplasia: a report of 24 adult cases. Circulation 1982; 65:384-398.
9. Fontaine G, Fontaliran F, Andrade F R, Velasquez E, Tonet J, Jouven X, Fujioka Y, Frank R. The arrhythmogenic right ventricle. Dysplasia versus cardiomyopathy. Heart Vessels 1995; 10:227-235.
10. Corrado D, Basso C, Thiene G, McKenna W J, Davies M J, Fontaliran F, Nava A, Silvestri F, Blomstrom-Lundqvist C, Wlodarska E K, Fontaine G, Camerini F. Spectrum of clinicopathologic manifestations of arrhythmogenic right ventricular cardiomyopathy/dysplasia: a multicenter study. J Am Coll Cardiol 1997; 30:1512-1520.
11. Lopez-Ayala J M, Pastor-Quirante F, Gonzalez-Carrillo J, Lopez-Cuenca D, Sanchez-Munoz J J, Oliva-Sandoval J R, Gimeno J R. Genetics of myocarditis in arrhythmogenic right ventricular dysplasia. Heart Rhythm 2015; 12:766-773.
12. Asimaki A, Tandri H, Duffy E R, Winterfield J R, Mackey-Bojack S, Picken M M, Cooper L T, Wilber D J, Marcus F I, Basso C, Thiene G, Tsatsopoulou A, Protonotarios N, Stevenson W G, McKenna W J, Gautam S, Remick D G, Calkins, Saffitz J E. Altered desmosomal proteins in granulomatous myocarditis and potential pathogenic links to arrhythmogenic right ventricular cardiomyopathy. Circ Arrhyth Electrophysiol 2011; 4:743-52.
13. Mendell J R, Moxley R T, Griggs R C, Brooke M R, Fenichel G M, Miller J P, King W, Signore K, Pandya S, Florence J, et al. Randomized, double-blind six-month trial of prednisone in Duchenne's muscular dystrophy. N Eng J Med 1989; 320:1592-1597.
14. Markham L W, Kinnett K, Wong B L, Benson W D, Cripe L H. Corticosteroid treatment retards development of ventricular dysfunction in Duchenne muscular dystrophy. Neuromuscul Disord 2008; 18:365-370.
15. Coghlan M P, Culbert A A, Cross D A, Corcoran S L, Yates J W, Pearce N J, Rausch O L, Murphy G J, Carter P S, Roxbee Cox K. Mills D, Brown M J, Haigh D, Ward R W, Smith D G, Murray K J, Reith A D, Holder J C. Selective small molecule inhibitors of glycogen synthase kinase-3 modulate glycogen metabolism and gene transcription. Chem Biol 2000; 7:793-803.

16. Asimaki A, Tandri J, Huang H, Halushka M K, Gautam S, Basso C, Thiene G, Tsatsopoulou A, Protonotarios N, McKenna W J, Calkins H, Saffitz J E. A new diagnostic test for arrhythmogenic right ventricular cardiomyopathy. New Eng J Med 2009:360:1075-84.
17. Garcia-Gras E, Lombardi R, Giocondo M R, Willerson J T, Schneider M D, Khoury D S, Marian A J. Suppression of canonical Wnt/beta-catenin signaling by nuclear plakoglobin recapitulates phenotype of arrhythmogenic right ventricular cardiomyopathy. J Clin Invest 2006; 116: 2012-21. PMCID: 1483165
18. Lombardi R, da Graca Cabreira-Hansen M, Bell A, Fromm R R, Willerson J T, Marian A J. Nuclear plakoglobin is essential for differentation of cardiac progenitor cells to adipocytes in arrhythmogenic right ventricular cardiomyopathy. Circ Res 2011; 109:1342-53.
19. Perkins N D. Post-translational modifications regulating the activity and function of the nuclear factor kappa B pathway. Oncogene 2006; 25:6717-6730.
20. Hayden M S, Ghosh S. Shared principles in NF-kappaB signaling. Cell 2008; 132:344-362.
21. Takada Y, Fang X, Jamaluddin M S, Boyd D D, Aggarwal B B. Genetic deletion of glycogen synthase kinase-3beta abrogates activation of IkappaBalpha kinase, JNK, Akt, and p44/p42 MAPK but potentiates apoptosis induced by tumor necrosis factor. J Biol Chem 2004; 279:39541-39554.
22. Fiol C J, Williams J S, Chou C H, Wang Q M, Roach P J, Andrisani O M. A secondary phosphorylation of CREB341 at Ser129 is required for the cAMP-mediated control of gene expression. A role for glycogen synthase kinase-3 in the control of gene expression. J Biol Chem 1994; 269:32187-32193.
23. Bullock B P, Habener J F. Phosphorylation of the cAMP response element binding protein CREB by cAMP-dependent protein kinase A and glycogen synthase kinase-3 alters DNA binding affinity, conformation, and increases net charge. Biochemistry 1998; 37:3795-3809.
24. Martin M, Rehani K, Jope R S, Michalek S M. Toll-like receptor-mediated cytokine production is differentially regulated by glycogen synthase kinase 3. Nat Immunol 2005; 6:777-784.
25. Rigato I, Bauce B, Rampazzo A, Zorzi A, Pilichou K, Mazzotti E, Migliore F, Marra M P, Lorenzon A, De Bortoli M, Calore M, Nava A, Daliento L, Gregori D, Iliceto S, Thiene G, Basso C, Corrado D. Compound and digenic heterozygosity predicts lifetime arrhythmic outcome and sudden cardiac death in desmosomal gene-related arrhythmogenic right ventricular cardiomyopathy. Circ Cardiovasc Genet 2013; 6:533-542.
26. Bhonsale A, Groeneweg J A, James C A, Dooij es D, Tichnell C Jongbloed J D, Murray B, to Riele A S, van den Berg M P, Bikker H, Atsma D E, de Groot N M, Houweling A C, van der Heij den J F, Russel S D, Doevendans P A, van Veen T A, Tandri H, Wilde A A, Judge D P, van Tintelen J P, Calkins H, Hauer R N. Impact of genotype on clinical course in arrhythmogenic right ventricular dysplasia/cardiomyopathy-associated mutation carriers. Eur Heart J 2015; 36:847-855.
27. Misra A, Haudek S B, Knuefermann P, Vallejo J G, Chen Z J, Michael L H, Sivasubramanian N, Olson E N, Entman M L, Mann D L. Nuclear factor-κB protects the adult cardiac myocyte against ischemia-induced apoptosis in a murine model of acute myocardial infarction. Circulation 2003; 108:3075-3078.
28. Ushach I, Zlotnik A. Biological role of granulocyte macrophage colony-stimulating factor (GM-CSF) and macrophage colony-stimulating factor (M-CSF) on cells of the myeloid lineage. J Leukoc Biol 2016; 100:481-489.
29. Wicks I P, Roberts A W. Targeting GM-CSF in inflammatory diseases. Nat Rev Rheumatol 2016; 12:37-48.
30. Dranoff G, Mulligan R C. Activites of granulocyte-macrophage colony-stimulating factor revealed by gene transfer and gene knockout studies. Stem Cells 1994; Supple 1:173-182.
31. Hamilton J A. GM-CSF as a target in inflammatory/autoimmune disease: current evidence and future therapeutic potential. Expert Rev Clin Immunol 2015; 11:457-465.
32. Anzai A, Choi J L, He S, Fenn A M, Nairz M, Rattik S, McAlpine C S, Mindur J E, Chan C T, Iwamoto Y, Tricot B, Wojtkiewicz G R, Weissleder R, Libby P, Nahrendorf M, Stone J R, Becher B, Swirski F K. The infarcted myocardium solicits GM-CSF for the detrimental oversupply of inflammatory leukocytes. J Exp Med 2017; 214:3293-3310.
33. Harada M, Van Wagoner D R, Nattel S. Role of inflammation in atrial fibrillation: pathophysiology and management. Circ J 2015; 79:495-502.
34. Dugo L, Collin M, Thiemermann C. Glycogen synthase kinase 3β as a target for the therapy of shock and inflammation. Shock 2007; 27:113-123.
35. Klamer G, Song E, Ko K H, O'Brien T A, Dolnikov A. Using small molecule GSK2β inhibitors to treat inflammation. Curr Med Chem 2010; 17:2873-2881.
36. Ridker P R, Everett B M, Thuren T, MacFayden J G, Chang W H, Ballantyne C, Forseca F, Nicolau J, Koenig W, Anker S D, Kastelein J J P, Cornel J H, Pais P, Pella D, Genest J, Cifkova R, Lorenzatti A, Forster T, Kobalava Z, Vida-Simiti L, Flather M, Shimokawa H, Ogawa H, Dellborg M, Rossi P R F, Troquay R P T, Libby P, Glynn R J, CANTOS trial group. Anti-inflammatory therapy with cankinumab for atherosclerotic disease. N Eng J Med 2017; 377:1119-1131.
37. MacRae C A, Taylor M R, Mestroni L, Moses J R, Ashley E A, Wheeler M T, Lakdawala N K, Hershberger R E, Ptaszynski M, Sandor V, Saunders M E, Oliver C, Lee P A, Judge D P. Phase 2 study of A797, an oral, selective p38 mitogen-activated protein kinase inhibitor, in patients with Lamin A/C-related dilated cardiomyopathy. e-poster, European Society of Cardiology Congress, August 27-31, Rome, Italy.
38. Sakai N, Wada T, Furuichi K, Iwata Y, Yoshimoto K, Kitagawa K, Kokubo S, Kobayashi M, Takeda S, Kida H, Kobayashi K, Mukaida N, Matsushima K, Yokoyama H. p38 MAPK phosphorylation and NF-κB activation in human crescentic glomerulonephritis. Nephrol Dial Transplant 2002; 17:998-1004.
39. Luo S F, Lin C C Chen H C, Lin W N, Lee I T, Lee C W, Hsiao L D, Yang C M. Involvement of MAPKs, NF-kappaB and p300 co-activator in IL-1beta-induced cytosolic phospholipase A2 expression in canine tracheal smooth muscle cells. Toxicol Appl Pharmacol 2008; 232: 396-407.
40. Vercammen E, Staal J, Van Den Broeke A, Haegman M, Vereecke L, Schotte P, Beyaert R. Prolonged exposure to IL-1beta and IFNgamma induces necrosis of L929 tumor cells via a p38MAPK-NKkappaB/NO-dependent mechanism. Oncogene 2008; 27:3780-3788.
41. Kopp W, Ghosh S. Inhibition of NF-kappa B by sodium salicylate and aspirin. Science 1994; 265:956-959.

42. Yuan M, Konstantopoulos N, Lee J, Hansen L, Li Z W, Karin M, Shoelson S E. Reversal of obesity- and diet-induced insulin resistance with salicylates or targeted disruption of Ikkbeta. Science 2001; 293:1673-1677.
43. Amann R, Peskar B A. Anti-inflammatory effects of aspirin and sodium salicylate. Eur J Pharmacol 2002:447-1-9.
44. Hariharan V, Asimaki A, Michaelson J E, Plovie E, MacRae C A, Saffitz J E, Huang H. Arrhythmogenic right ventricular cardiomyopathy mutations alter shear response without changes in cell-cell adhesion. Cardiovasc Res 2014; 104:280-289.
45. Asimaki A, Protonotarios A, James C A, Chelko S P, Tichnell C, Murray B, Tsatsopoulou A, Anastasakis A, to Riele A, Kleber A G, Judge D P, Calkins H, Saffitz J E: Characterizing the molecular pathology of arrhythmogenic cardiomyopathy in patient buccal mucosa cells. Circ Arrhythm Electrophysiol. 2016; 9: e003688.
46. Zhan T, Rindtorff N, Boutros M: Wnt signaling in cancer. Oncogene. 2017; 36:1461-1473.
47. Campbell J J, Perkins N D. Regulation of NF-kappaB function. Biochem Soc Symp. 2006; 73:165180.
48. Syed F, Diwan A, Hahn H S. Murine echocardiography: a practical approach for phenotyping genetically manipulated and surgically modeled mice. J Am Soc Echocardiogr. 2005; 18:982-990.
49. Kim C, Wong J, Wen J, Wang S, Wang C, Spiering S, Kan N G, Forcales S, Puri P L, Leone T C, Marine J E, Calkins H, Kelly D P, Judge D P, Chen H S. Studying arrhythmogenic right ventricular dysplasia with patient-specific iPSCs. Nature. 2013; 494:105-110.
50. Bhattacharya S, Burridge P W, Kropp E M, Chuppa S L, Kwok W M, Wu J C, Boheler K R, Gundry R L. High efficiency differentiation of human pluripotent stem cells to cardiomyocytes and characterization by flow cytometry. J Vis Exp. 2014; 91:52014.
51. McKoy G, Protonotarios N, Crosby A, Tsatsoupoulou A, Anastasakis A, Coonar A, Norman M, Baboonian C, Jeffery S, McKenna W J. Identification of a deletion in plakoglobin in arrhythmogenic right ventricular cardiomyopathy with palmoplantar keratoderma and woolly hair (Naxos disease). Lancet. 2000; 355:2119-2124.
52. Basso C, Thiene G, Corrado D, Angelini A, Nava A, Valente M. Arrhythmogenic right ventricular cardiomyopathy. Dysplasia, dystrophy or myocarditis? Circulation. 1996; 94:983-991.
53. Lazzerini P E, Capecchi P L, Laghi-Pasini F. Systemic inflammation and arrhythmic risk: lessons from rheumatoid arthritis. Eur Heart J. 2017; 38:1717-1727.
54. Miller S C, Huang R, Sakamuru S, Shukla S J, Attene-Ramos M S, Shinn P, Van Leer D, Leister W, Austin C P, Xia M. Identificatioin of known drugs that act as inhibitors of NF-kappaB signaling and their mechanism of action. Biochem Pharmacol. 2010; 79:1272-1280.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a human subject with arrhythmogenic cardiomyopathy (ACM), the method comprising:
(a) identifying a human subject as having or at risk of developing ACM; and
(b) administering to the human subject a therapeutically effective amount of an anti-interleukin-1β (IL-1β) antibody selected from the group consisting of canakinumab, APX002, and XOMA052.

2. The method of claim 1, wherein the anti-IL-1β antibody is canakinumab.

3. The method of claim 1, wherein the anti-IL-1β antibody is APX002.

4. The method of claim 1, wherein the anti-IL-1β antibody is XOMA052.

5. The method of claim 1, wherein step (a) comprises determining that the human subject has a desmoglein-2 (DSG2) deficiency.

6. The method of claim 5, wherein determining that the human subject has a desmoglein-2 (DSG2) deficiency comprises determining that the human subject has a mutation in the DSG2 gene, or by measuring the level of DSG2 protein.

7. The method of claim 1, wherein step (b) comprises injecting the IL-1β antibody in the human subject.

* * * * *